United States Patent [19]

Messenger et al.

[11] Patent Number: 5,733,787
[45] Date of Patent: Mar. 31, 1998

[54] METHOD FOR THE DETECTION OF CREATININE

[75] Inventors: Koleen K. Messenger, Granger; Carol A. Miller; Meitak Teresa Yip, both of Elkhart, all of Ind.

[73] Assignee: Bayer Corporation, Elkhart, Ind.

[21] Appl. No.: 664,869

[22] Filed: Jun. 17, 1996

[51] Int. Cl.$^6$ ............................................. G01N 33/70
[52] U.S. Cl. .................... 436/98; 436/80; 436/164; 436/169; 436/904; 435/4; 435/28; 422/56
[58] Field of Search ................... 436/98, 108, 80, 436/164, 166, 169, 174, 904; 435/4, 28; 422/55, 56

[56] References Cited

U.S. PATENT DOCUMENTS

| | | | |
|---|---|---|---|
| 5,173,431 | 12/1992 | Pugia et al. | 436/86 |
| 5,374,561 | 12/1994 | Pugia | 436/98 |
| 5,385,847 | 1/1995 | Yip et al. | 436/98 X |
| 5,464,777 | 11/1995 | Yip | 436/98 |
| 5,527,708 | 6/1996 | Blass | 436/98 |

*Primary Examiner*—Maureen M. Wallenhorst
*Attorney, Agent, or Firm*—Jerome L. Jeffers

[57] ABSTRACT

Disclosed is a method for the determination of creatinine in urine which involves contacting a urine test sample with a reagent system containing $Cu^{+2}$, a hydroperoxide and an oxidizible dye which provides a detectable response when oxidized in the presence of a pseudoperoxide. The reagent system also includes a buffer to maintain the urine's pH within the range of 6.6 to 8.0 and a chelating agent for the cupric ions to prevent oxidation of the dye in the absence of creatinine.

15 Claims, 3 Drawing Sheets

METHOD FOR THE DETECTION OF CREATININE

BACKGROUND OF THE INVENTION

Peroxidase is an enzyme that catalyzes the oxidation of various compounds, such as phenols and amines, by peroxides. In addition, particular compounds have been termed pseudoperoxidases because they behave in a manner similar to the peroxidase enzyme by liberating oxygen from hydroperoxides and transferring the oxygen to certain acceptor compounds. Thus, the pseudoperoxidases are enzyme-like in that they catalyze, or otherwise participate in, reactions between peroxides and oxidizable compounds. The pseudoperoxidases, which include hemoglobin and its derivatives, are regarded as peroxidatively active substances. For example, in the assay of urine for glucose, the enzyme glucose oxidase, in the presence of oxygen, first converts the glucose in the urine to gluconic acid and hydrogen peroxide after which the peroxidase enzyme which is included in the assay system catalyzes the interaction between the hydrogen peroxide (hydroperoxide) and an oxidizable dye compound, such as O-tolidine or tetramethylbenzidine, to cause the dye, which is colorless in its reduced state, to become colored thereby providing a detectable response. The degree and intensity of the colored response are directly proportional to the amount of hydrogen peroxide generated by the glucose conversion, provided there is sufficient peroxidase present to catalyze the oxidation of the dye.

Similarly, a peroxidatively active substance such as hemoglobin or a derivative thereof can catalyze the interaction between a hydroperoxide and an oxidizable dye. In such interactions, the peroxidatively active substance imitates the peroxidase and catalyzes the interaction between the oxidizable dye and the hydroperoxide. The resulting interaction provides a detectable response, such as a color transition, wherein the intensity of the response is indicative of the concentration of the peroxidatively active substance.

Creatinine is the end metabolite when creatine becomes creatine phosphate and is used as an energy source for muscle contraction. The creatinine produced is filtered by the kidney glomeruli and then excreted into the urine without reabsorption. The determination of creatinine in body fluids is useful for diagnosing muscle diseases such as nephritis and renal insufficiency. The first practical test for the determination of creatinine in urine, known as the Jaffé method, involves the formation of the red-yellowish brown colored creatinine picrate by the bonding of picric acid and creatinine in an alkaline solution. A more recent method for creatinine determination is reported by Benedict and Behre in *J. Biol. Chem.*, 113: 515 (1936) which involves the reaction of 3,5-dinitrobenzoic acid with creatinine in an alkaline medium. Each of these reactions requires a high pH, i.e. on the order of 12–13, in order to deprotonate the creatinine, so that the system can operate properly. Strongly basic substances such as alkali and alkaline earth metal hydroxides are typically used to maintain a suitable high pH in these reagent systems. Operating at these high pH levels presents various difficulties, especially when an absorbant carrier such as filter paper or a porous film is used as carrier for the reagent system since, upon introduction of the alkali, the carrier tends to become brittle and it becomes difficult to obtain even distribution of the alkali throughout the carrier matrix. Furthermore, when the reagents are applied to the carrier in the form of a solution and the solvent evaporated to leave a dry residue, the dried alkali does not readily solubilize when contacted with a fluid such as urine which is being examined for creatinine concentration.

The difficulty encountered in dealing with the high alkalinity required for the successful use of these creatinine tests has led to the search for alternative tests which do not require these high pH values. One such test is disclosed in U.S. Pat. No. 5,374,561 in which a urine sample is contacted with cupric ions, a hydroperoxide, an oxidizable dye which provides a colored response in the presence of oxygen free radicals and a pseudoperoxidase. The reagent system contains citrate as a chelating agent to prevent urine components other than creatinine from complexing with the cupric ions. In this system, it appears that the complex formed between the cupric ion and creatinine acts as a pseudoperoxidase due to its ability to oxidize the redox indicator, thereby causing it to assume the colored form of the oxidized redox indicator. The '561 patent illustrates good results with this system using succinic acid as buffer. However, it has now been discovered that the succinic acid buffered system is not truly satisfactory for use in creatinine determination in a broad selection of urines because it does not possess sufficient buffering capacity to provide consistent results with urine samples of varying pH and specific gravities. More particularly in this system, the reactivity is very sensitive to the pH of the reaction mixture. Within the pH range tested, i.e. pH 5.4 to 7.5, the reactivity of the system increases with decreasing pH. Furthermore, a lower pH would increase the hemoglobin interference since hemoglobin can also act as a pseudoperoxidase and cause positive bias on the assay result and the activity of hemoglobin increases with decreasing pH. Accordingly, it is very important to keep the test system at a specified pH (between 6.6 to 8.0) such that the interference of hemoglobin is minimized and the effect from the variation of the pH of the test solution is reduced. There are two important aspects in controlling the pH of the system. One is to have buffering agents with pKa's within the operating pH range, and the other is to have sufficient buffer capacity to overcome the pH/SG (specific gravity) variations of test solutions. The SG effect is significant because as urine SG increases, its ionic strength also increases.

Accordingly, it is an object of the present invention to provide a system for the determination of creatinine in urine which does not require the maintenance of a highly alkaline reagent system and which accurately determines creatinine concentration in both high and low pH and specific gravity urines.

SUMMARY OF THE INVENTION

The present invention involves a method for the determination of the concentration of creatinine in urine which comprises contacting a urine test sample with a reagent system comprising $Cu^{+2}$ ions, a hydroperoxide and an oxidizable dye which provides a detectable response when oxidized in the presence of a pseudoperoxidase. The reagent system further comprises a buffer having a suitable pKa and present in sufficient quantity to maintain the urine sample's pH within the range of from 6.6 to 8.0 upon contact therewith and a chelating agent for the cupric ions to prevent oxidation of the dye in the absence of creatinine.

DESCRIPTION OF THE INVENTION

Figure 1:
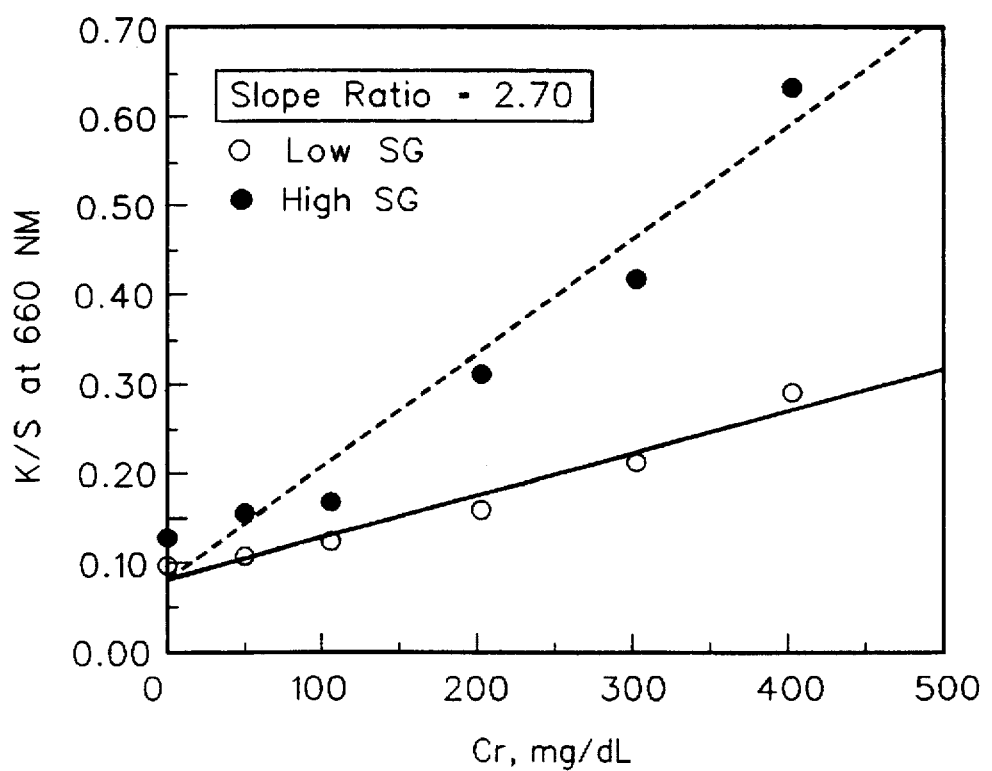
FIG. 1 depicts the results of using succinic acid as the buffer system in the method according to the invention with both low and high specific gravity urine samples in accordance with Example 1.

As is more fully described in the aforementioned U.S. Pat. No. 5,374,561; it is believed that the following set of equations account for the ability of cupric ion in combination with a chelating agent such as citrate, a peroxide and a redox indicator such as tetramethylbenzidine (TMB) to indicate the presence of creatinine in urine.

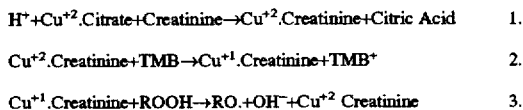

Reaction 1 represents the formation of the $Cu^{+2}$. creatinine complex from its resting state. Reaction 2 represents the oxidation of the TMB dye by the transfer of 1 electron from the TMB to the $Cu^{+2}$. Creatinine complex to produce the non-reactive $Cu^{+1}$ form. Reaction 3 is the regeneration step whereby the $Cu^{+1}$ complex loses an electron to the peroxide to regenerate the $Cu^{+2}$.

In this system, the source of cupric ion may be any soluble copper salt whose anion does not detrimentally interact with the reaction for the colorimetric detection of creatinine. Suitable salts include copper sulfate, nitrate, hydroxide, phosphate, iodide, chloride, bromide, acetate or oxalate. Other cupric salts may be used provided that they allow formation of the $Cu^{+2}$. creatinine complex. Those salts whose anion binds too strongly to copper ions will not allow the copper$^{+2}$/creatinine complex to be formed. Accordingly, $Cu^{+2}$ complexes such as those formed between cupric ions and EDTA, HEDTA, EGTA and DTPA would not release sufficient $Cu^{+2}$ for formation of the $Cu^{+2}$/creatinine complex. Citrate and sulfate salts have the lowest blank reactivity and, accordingly, they are preferred. Chelating agents other than citrate may be used provided that it forms a copper$^{+2}$ complex having a binding constant which is lower than that of creatinine but high enough to complex with copper in order to prevent free copper (II) from oxidizing the hydroperoxide/oxidizable dye system. Salts which oxidize the dye in the absence of creatinine are, of course, not suitable. For example, salts such as cupric 2,2'-bipyridine can cause significant oxidation of TMB in the absence of creatinine, and are, therefore unsuitable for use in the present invention.

Typically, the concentration of cupric ion will be from 5 to 80 mM since the reference range of creatinine in urine is 1.3 to 36 mM. The couprous ion tends to cause background interference due to oxidation of the dye in the absence of creatinine. Accordingly, $Cu^{+1}$ salts cannot be used.

The concentration of copper ion and the ratio of $Cu^{+2}$/citrate complex are very important in this assay system since they affect the performance of the system with respect to its citrate resistance. It was found that citrate causes significant inhibition interference in the assay; and, since urine may contain as much as 6 mM citrate, the citrate ion competes with creatinine to complex with the copper (II) ion. The $Cu^{+2}$/creatinine complex oxidizes TMB in the presence of DBDH while the $Cu^{+2}$/citrate complex does not. As shown in Table 1 which is incorporated into Example VI, it was found that the increase of both $Cu^{+2}$ and citrate concentrations in formula A from 16/27 to 30/50 mM increased the citrate interference resistance thereby reducing the citrate effect. Referring again to Table 1, the citrate inhibition effect was reduced to 16.3% and 18.6% in formula A for solutions containing citrate at 10 and 20 mM respectively as compared to only 53.6% and 58.5% in formula B and 66.3% and 86.5% in formula C. In a more extensive study, the results of which are summarized in Table 2, it was found that while keeping the copper concentration at 30 mM and increasing the concentration of citrate to 100 mM (increasing the citrate/Cu ratio to 3.3) reduced the citrate effect to 2% which is a great improvement in terms of citrate resistance. Accordingly, in carrying out the present invention, it is preferred that the citrate to $Cu^{+2}$ ratio be in the range of 0.5 to 3.5 wherein the $Cu^{+2}$ concentration is from 5 to 80 mM and the citrate concentration is 3 to 280 mM.

Suitable oxidizable indicators for use in the present invention include, for example, benzidine; o-tolidine; a 3,3',5,5'-tetraalkylbenzidine wherein the alkyl group includes from one to about six carbon atoms; o-dianisidine; 2,7-diaminofluorence; bis-(N-ethylquinol-2-one)-azine; (N-methylbenzthiazol-2-one)-(1-ethyl-3-phenyl-5-methyltriazole-2-one)-azine or combinations thereof.

Suitable hydroperoxides for use in the present invention include cumene hydroperoxide; 5-butyl hydroperoxide; diisopropylbenzene hydroperoxide; 1-hydroxycyclohexane-1-hydroperoxide; 2,5-dimethylhexane-2,5-dihydroperoxide; paramenthane hydroperoxide; 1,4-diisopropylbenzene monohydroperoxide; p-t-butylisopropylbenzene hydroperoxide; 2-(α-hydroperoxyisopropyl)-6-isopropylnaphthalene; tetralin hydroperoxide or combinations thereof.

The '561 patent describes the use of succinic acid buffer to maintain a urine sample at pH 7.0. This system worked well to provide a fairly linear dose/response curve of creatine concentration-vs-reflectance at 660 nm over a range of creatinine concentrations of from 0 to 250 mg/dL. The succinic acid buffered urine worked well in this experiment, but, as can be determined from FIG. 1, the system did not provide consistent results over a range of high and low specific gravity. However, it has now been discovered that succinic acid is not a suitable buffer in all situations due to fluctuations in the pH and specific gravity (SG) of urine samples that need to be tested for creatinine. This is the case because the succinic acid at 250 mM concentration does not have the buffering capacity to resist the variation of pH and high ionic strength of some urine samples. The results in such cases are that the reagent pads will no longer be held at the desired pH such as 7.0. For example, with a urine sample of pH 5.6 and high SG the pH of the reaction system would be reduced below the desired minimum of 6.6 and, with a urine sample of pH 8.5 and high SG the pH of the reaction system would be elevated to a level higher than the desired maximum of 8.0. The solution to this problem lies in the use of a buffer which has the capability, when provided in sufficient quantity, to maintain the pH of the urine test sample at a pH in the range of from 6.6 to 8.0 during the course of the colorimetric creatinine determination. The use of such a buffer system provides consistent results regardless of the SG of the urine sample being tested because a well buffered system shows little change in pH when interacting with other materials having a different pH. The buffering ability of a weak acidic or basic group is limited to approximately the range of pH=pKa±1 with the greatest effect being at a pH equal to the pKa. This is one of the most important factors in choosing a buffer for a particular application. Other important considerations such as ionic strength, the compatibility of the buffer compound to the reaction system and its solubility. According to the Debye-Huckel equation, the ionic strength should be included in calculating the "practical pKa" according to the following equation:

$$pKa'=pKa-(2n-1)[(0.5*I^{1/2})/(1+I^{1/2})-0.1I]$$

where I is the ionic strength of the solution=½$\Sigma cZ^2$ where c is the concentration in molar z is the charge. The buffer capacity can be expressed as a quantitative measure of the buffering ability of a solution, i.e. the buffer unit or buffer value β. The maximum amount of strong acid or base needed to change the pH of the buffer system by a small amount, $\beta_{max}$, is given as:

$$\beta_{max}=0.576 \times C$$

where C is the molar concentration. Therefore, if the buffer system is in the good buffer range, the buffer capacity is directly proportional to its concentration. According to the above principle, in order to provide a good buffer at pH 7.0, a buffer reagent with a pKa=pH±1=6.0 to 8.0 should be used. Succininc acid has a pKa of 5.6 which provides good buffering only in the range of 4.6 to 6.6. Glycerol-2-phosphate, on the other hand, has a pKa value of 6.65. Its good buffering range is 5.65 to 7.65, and therefore at a concentration of 0.5M to 0.75M is a more suitable buffer than 0.25M succinic acid.

Buffers suitable for use in the present invention are typically those which have a pKa in the range of 6.6 to 8.0 and preferably from 6.7 to 7.4. This provides a pH which includes the best balance of sensitivity, stability, resistance to temperature changes, ascorbate interference as well as interferences from citrate and hemoglobin. In addition, such a buffer system gives accurate results when assaying urine samples with highly variable pH and specific gravity values. Among the buffers which fall into this category are phosphate, glycerol-2-phosphate, maleic acid, 3-N-morpholinopropanesulfonic acid (MOPS), cacodylic acid, 3,3-dimethylglutaric acid, carabonic acid, 4-hydroxymethylimidazole, Bis-tris[bis-(2-hydroxyethyl)-imino]-tris [(hydroxymethyl)methane], orthophosphorous acid, dimethylaminoethylamine, ADA (N-(2-acetamido) iminodiacetic acid, pyrophosphoric acid, N, N'-bis(3-sulphopropyl)ethylenediamine, piperazine-N,N'-bis(2-ethanesulphonic acid)), 1,3-bis[tris(hydroxymethyl)methylamino]propane, ethylenediamine, N-(2-acetamido)-2-aminoethanesulphonic acid, imidazole, (2-aminoethyl) trimethylammonium chloride, N,N-bis(2-hydroxyethyl)-2-aminoethanesulphonic acid, 3,6-endomethylene-1,2,3,6-tetrahydrophthalic acid, 2.3-dihydroxypropyl-tris-(hydroxymethyl)methylamine, 2,4,6-trimethylpyridine, N-tris(hyddroxymethyl)methyl-2-aminoethanesulphonic acid, 4-methylimidazole, N-2-hydroxyethylpiperazine-N'-2-ethanesulphonic acid, N-ethylmorpholine, triethanolamine, mono-tris-2-hydroxyethylimino-tris(hydroxymethyl) methane, triisopropylamine, 5,5-diethylbarbituric acid, N-2-hydroxyethylpiperazinepropanesulphonic acid, glycylglycine, phenyl phosphate, nitrophenyl phosphate, naphthyl phosphate, diphenyl phosphate, phenyl phosphonic acid, aminoethyl phosphonic acid, ethyl phosphonic acid, carboxyethyl phosphonic acid, ethyl phosphate, aminoethyl phosphate, glycerol phosphate, phytic acid, 6-glucose phosphate, and 1-glucose phosphate or combinations thereof. The buffer concentration range is typically from 250 mM to 1000 mM and preferably from 300 mM to 750 mM. These buffers, when used in sufficient quantity, will maintain the pH of the reagent system within the desired level over the range of urine SG one would expect to encounter during clinical testing.

In the practice of this invention, the creatinine assay can be performed in either the wet or dry (test strip) format. In carrying out the assay, the urine test sample is mixed with the copper salt, e.g. cupric sulfate or cupric citrate, the redox dye and the hydroperoxide and the buffer system through the use of reagent strips bearing the reagent system or a solution of the reagents. Reagent strips are prepared in the conventional manner of dipping an absorbant carrier into an aqueous solution of the cupric salt and a buffer, drying the carrier and then dipping it into an organic solution of the dye and hydroperoxide with subsequent drying. Suitable materials from which the test strip can be fabricated include felt, porous ceramic strips and woven or matted glass fibers such as those described in U.S. Pat. No. 3,846,247. Also suitable are wood, cloth, sponge material and argillaceous substances such as those described in U.S. Pat. No. 3,552,928. Filter paper is the preferred material.

The concentration of cupric salt in the aqueous dip solution will normally range from 5 to 80 mM. When the buffer used is glycerol-2-phosphate, its concentration in the dip solution will normally range from 250 to 1000 mM in order to provide a reagent strip which will maintain the desired pH when dipped in a urine test sample. The concentration of the redox dye in the organic dip solution will normally range from 10 to 150 mM with 30 to 90 mM being preferred whereas the hydroperoxide will range in concentration from 18 to 270 mM with 54 to 162 mM being preferred. The ratio of DBDH to TMB is optimal at 1.8.

The method of practicing the present invention is further illustrated by the following examples:

Test strips for the determination of creatinine in aqueous solution were prepared using Whatman BP87 and 3 MM filter paper. They were prepared by a two dip process in which the first dip was an aqueous solution containing the buffer, copper sulfate as the source of cupric ion and citric acid. The solution was prepared by accurately weighing the buffering reagents, copper sulfate, citric acid and other reagents into a beaker. After addition of water, the resulting mixture was stirred on a magnetic stirring plate at ambient temperature until all solids were dissolved. Sodium dodecyl sulfate (SDS) was prepared separately as a 50× concentrated solution to improve the color formation and enhance the reactivity of the system and was added to the buffer solution. The pH of the solution was then adjusted to the desired level using 10N and 1N sodium hydroxide solutions. Water was added to the desired volume whereupon the final pH was measured and recorded.

The second dip was an organic solution (acetonitrile or ethanol as solvent) containing tetramethylbenzidine (TMB) as dye and diisopropylbenzene dihydroperoxide (DBDH) as the hydroperoxide. The dye and hydroperoxide were accurately weighed into a volumetric flask followed by addition of the solvent to provide a mixture which was stirred on a magnetic stirring plate at ambient temperature until all of the solid was dissolved. Organic solvent was then added QS to volume.

Strips of filter paper (8×2 inches) were clamped to a frame and dipped in the first (aqueous) solution and dried in a convection oven for 5 minutes at 50° C. This procedure was repeated with the second (solvent) solution. After impregnation and drying, the strips were stored with desiccant in sealed drums and later mounted on acrylic-based adhesive and polystyrene backing.

The strips were evaluated by providing two sets of test solutions having different SG and pH values. The test solutions were designed to mimic the high and low of SG and pH values found in urine. The high SG (HSG) solution had a SG of 1.020 and a pH of 5.6 whereas the low SG (LSG) solution had a SG of 1.005 and a pH of 7.2. Each of the test solutions were dosed with five levels of creatinine; i.e. 0, 50, 100, 200 and 300 mg/dL.

To perform an assay, about 0.8 mL of test solution was added to a test tube. A strip was dipped into the solution at the same time as the start button on a CLINITEK®-10 reflectance spectrophotometer was pressed. The strip was placed on the instrument's read table after dipping in the test solution and an instrumental reading, which was provided by the instrument as a K/S value derived from the reflectance measured, was reported as the response signal. Replicates of five tests were performed on all test solutions.

EXAMPLE I

The first set of strips, in which succinic acid was used as the buffer, was prepared by the double dip procedure using the following dip solutions:

| First Dip: | Copper sulfate | 16 mM |
|---|---|---|
| | Citric acid | 27 mM |
| | Succinic acid | 250 mM |
| | 1N NaOH to adjust to pH 6.9 | |
| Second Dip: | TMB | 80 mM |
| | DBDH | 90 mM |
| | Acetonitrile solvent | |

Evaluations with LSG and HSG test solutions indicated that the SG/pH effects were significant as indicated by FIG. 1. In FIG. 1, the results of using succinic acid at 250 mM as the buffer system are shown and a significant pH/SG effect was observed. The effect is expressed as the ratio of K/S of the slope of high SG to low SG. The ratio in this case is 2.70 showing that the pH/SG effect is 170%.

EXAMPLE II

A second set of test strips, using glycerol-2-phosphate, disodium and sodium chloride as the buffer system was prepared from the following dip solutions:

| First Dip: | Copper sulfate | 16 mM |
|---|---|---|
| | Citric acid | 27 mM |
| | glycerol-2-phosphate, disodium | 1000 mM |
| | sodium chloride | 500 mM |
| | 10N NaOH to adjust to pH 6.8 | |
| Second Dip: | TMB | 80 mM |
| | DBDH | 90 mM |
| | Acetonitrile | |

Figure 2:
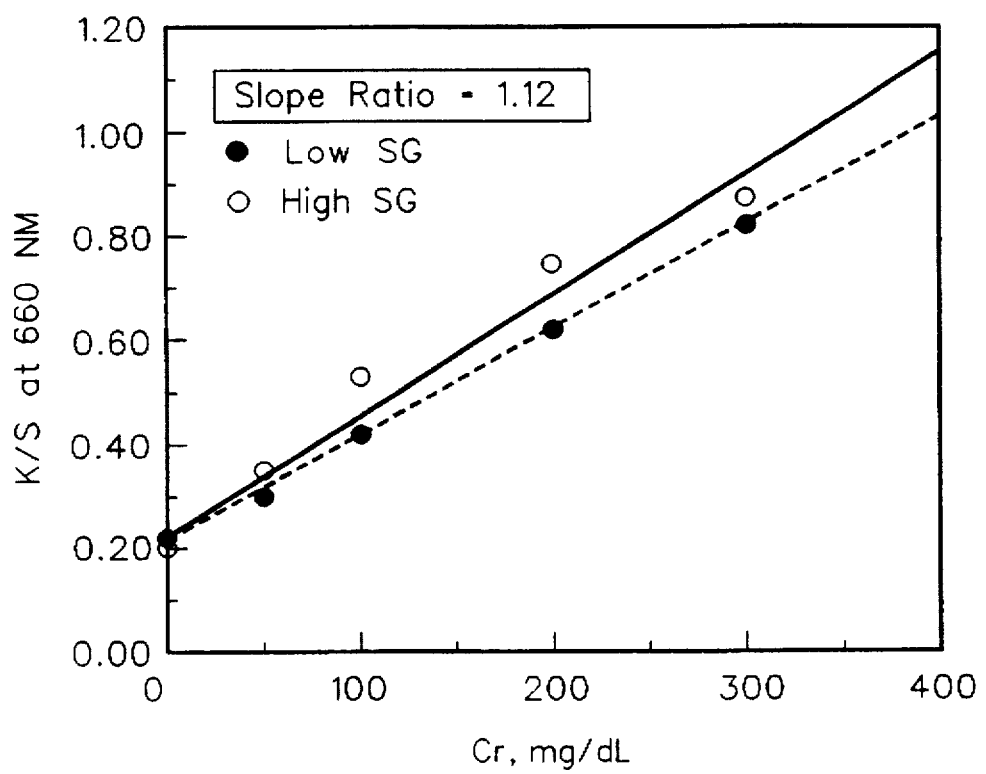
FIG. 2 depicts the results of using glycerol-2-phosphate as the buffer system in the method according to the invention with both low and high specific gravity urine samples in accordance with Example 2.

The test strips were prepared by the previously described double dip method and evaluated as before. The results of this evaluation are graphically set out in FIG. 2. Referring to FIG. 2, the dose response (expressed as K/S) slope ratio of the HSG sample over the LSG sample is 1.12. This is preferable to the ratio of 2.70 obtained using succinic acid as the sole buffer because by using a better buffer system, the pH/SG effect is significantly reduced. The slope ratio is 1.12 or the pH/SG effect is 12%.

EXAMPLE III

A third set of test strips was prepared using the following dip solutions:

| First Dip: | Copper sulfate | 30 mM |
|---|---|---|
| | Citric acid | 50 mM |
| | Glycerol-2-phosphate, disodium | 750 mM |
| | SDS | 0.1% |
| | 10N NaOH to adjust to pH 7.18 | |
| Second Dip: | TMB | 33 mM |
| | DBDH | 60 mM |
| | Ethanol | |

Figure 3:
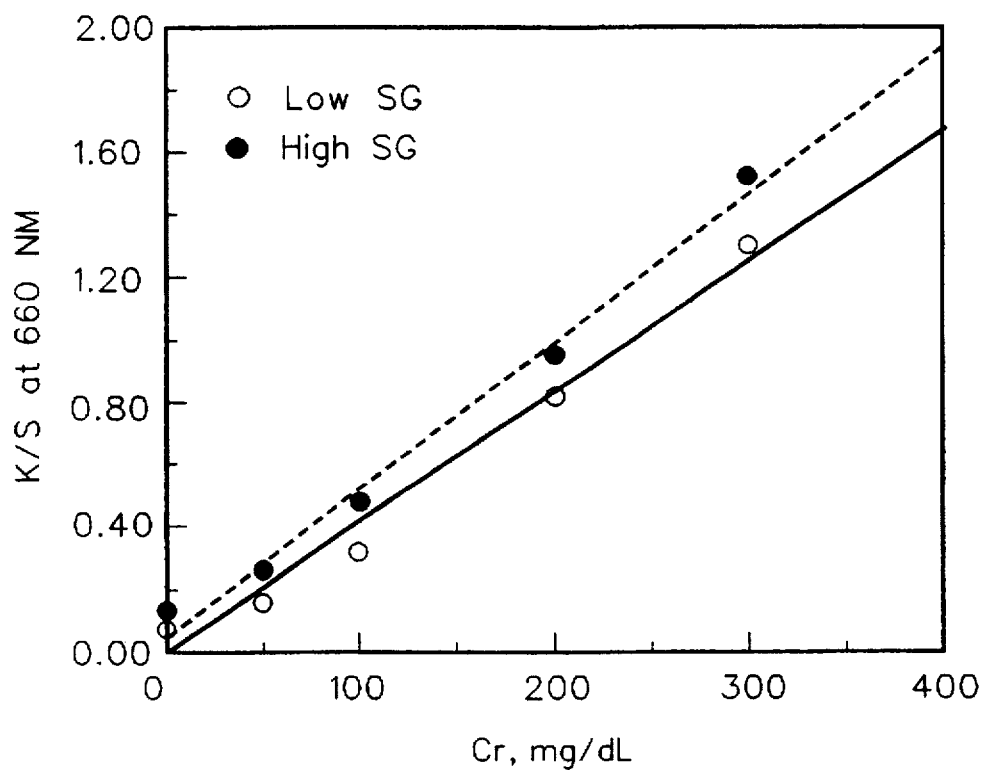
FIG. 3 depicts the results of using glycerol-2-phosphate as the buffer system in the method according to the invention with both low and high specific gravity urine samples in accordance with Example 3.

The dose responses obtained using strips prepared from these dip solutions are graphically represented in FIG. 3.

EXAMPLE IV

A fourth set of test strips was prepared using the following two dip solutions in which MOPS is 3(N-morpholino) propanesulfonic acid which has a pKa value of 7.2. By using the combination of buffer reagents a wider range of pH can be covered, i.e. glycerol-2-phosphate (pKa 6.65) covered pH 5.65 to 7.65 and MOPS covered 6.2 to 8.2 providing a total pH range of 5.65 to 8.2 which is the pH range found in urine samples.

| First Dip: | Copper sulfate | 16 mM |
|---|---|---|
| | Citric acid | 27 mM |
| | Glycerol-2-phosphate, disodium | 500 mM |
| | MOPS | 500 mM |
| | Triisopropylamine borate | 120 mM |
| | 10N NaOH to adjust to pH 7.15 | |
| Second Dip: | TMB | 33 mM |
| | DBDH | 60 mM |
| | Ethanol | |

Testing of strips made using these dip solutions demonstrated that good dose response with little pH/SG effect could be obtained.

EXAMPLE V

In a fifth run, strips were prepared from the following dip solutions:

| First Dip: | Copper sulfate | 16 mM |
|---|---|---|
| | Citric acid | 27 mM |
| | Glycerol-2-phosphate, disodium | 300 mM |
| | MOPS | 300 mM |
| | SDS | 0.04% |
| | Plasdone | 2.5% |
| | 10N NaOH to adjust to pH 7.15 | |
| Second Dip: | TMB | 33 mM |
| | DBDH | 60 mM |
| | Ethanol | |

Strips prepared using these dip solutions were more stable due to the inclusion of plasdone.

EXAMPLE VI

During the research which led to the development of this invention, it was discovered that citrate in the test solutions caused a negative bias in the creatinine determination method. More particularly, the citrate interfered with the assay such that the recovery of analyte (creatinine) was lower than the true concentration. It was found that increasing the concentration of the $Cu^{+2}$/citrate complex increased the resistance to interference of citrate from the urine test sample. A study was performed on three creatinine reagent strip formulations characterized as A, B and C. In the study, a standard curve was first generated and low specific gravity (LSG) test solutions (pH 7.2) containing 100 mg/dL (95 mg/dL as the final concentration) of creatinine spiked with 200 mg/dL and 400 mg/dL of citric acid solution (pH of citric acid solution was 7.2) were assayed in quartet. The amount of creatinine in the test solutions was determined from the standard curve and the % recovery calculated. The results for formulation A, B and C are set out in Table 1. Formulation A, with the higher copper/citrate complex concentration exhibited the best citrate resistance, 83.8% of creatinine detected at 200.5 mg/dL and 81.4% at 401 mg/dL citrate as compared to 46.4% and 41.5% for B and 33.7% and 13.5% for C.

TABLE 1

| Formulation | A | B | C |
| --- | --- | --- | --- |
| Buffer | glycerol-2-phosphate, 750 mM | glycerol-2-phosphate/MOPS 500/500 mM | glycerol-2-phosphate 750 mM |
| Cu/citrate, mM | 30/50 | 16/27 | 16/27 |
| (citrate/Cu ratio) | (1.7) | (1.7) | (1.7) |
| Expected Cr, mg/dL | 95.0 | 95.0 | 95.0 |
| Citrate, mM | 10 | 10 | 10 |
| Recovered Cr, mg/mL | 79.6 | 44.1 | 32.0 |
| % recovered | 83.75% | 46.38% | 33.69% |
| Citrate effect | 16.3% | 53.6% | 66.3% |
| Citrate, mM | 20 | 20 | 20 |
| Recovered Cr, mg/mL | 77.3 | 39.4 | 12.8 |
| % recovered | 81.4% | 41.5% | 13.5% |
| Citrate effect | 18.6% | 58.5% | 86.5% |

From Table 1 it can be determined that citrate interference can be reduced by increasing the total amount of $Cu^{+2}$ and citrate.

EXAMPLE VII

Strips were prepared as before using various concentrations of cupric ion and citrate. Formulations containing copper sulfate varied from 30–80 mM whereas citrate concentration varied from 50 to 120 mM. The pH/SG effects were investigated. The pH/SG effect is the interference of pH/SG with the determination of creatinine concentration or $$pH/SG\ effect = \frac{(observed\ Cr\ concentration\ for\ LSG - observed\ Cr\ concentration\ for\ HSG)}{observed\ Cr\ concentration\ at\ HSG} \times 100$$

where Cr=creatinine. The results of this study, in which each of the strips were tested on urine samples containing 0, 30, 100, 200 and 300 mg/dL creatinine and readings taken on a reflectance spectrometer which expressed activity in terms of K/S; are set out in Table 2.

TABLE 2

| Formula | D | E | F | G | H | I | J |
| --- | --- | --- | --- | --- | --- | --- | --- |
| $CU^{+2}$, mM | 30 | 30 | 30 | 30 | 60 | 60 | 80 |
| Citrate, mM | 50 | 60 | 80 | 100 | 50 | 120 | 50 |
| Citrate/Cu ratio | 1.7 | 2.0 | 2.7 | 3.3 | 0.8 | 2.0 | 0.6 |
| Cr, mg/dL | | | | K/S activity | | | |
| 0 | 0.098 | 0.102 | 0.078 | 0.075 | 0.918 | 0.080 | 1.075 |
| 30 | 0.146 | 0.151 | 0.095 | 0.093 | 1.228 | 0.106 | 1.303 |
| 100 | 0.298 | 0.276 | 0.167 | 0.149 | 1.573 | 0.179 | 1.638 |
| 200 | 0.614 | 0.594 | 0.316 | 0.278 | 2.065 | 0.344 | 2.071 |
| 300 | 1.005 | 0.954 | 0.526 | 0.443 | 2.378 | 0.558 | 2.532 |
| SG/pH effect | 20% | 14% | 16% | 12% | 4% | 17% | 8% |
| Citrate effect 6 mM citrate | 7% | 12% | 8% | 2% | 33% | 25% | — |

From Table 2 it can be determined that by using an appropriate buffer system, the pH/SG effect was greatly reduced from 170% to less than 20%. In formulation H, the pH/SG formulation was reduced to only 4%.

We claim:

1. A method for the detection of creatinine in urine which comprises contacting a urine test sample with a reagent system comprising cupric ions, a hydroperoxide and an oxidizable dye which provides a detectable response when oxidized in the presence of a pseudoperoxide together with a buffer having a pKa in the range of 6.6 to 8.0 and in sufficient quantity to maintain the urine sample's pH within the range of from about 6.6 to 8.0 upon contact therewith regardless of the specific gravity of the urine test sample and a chelating agent for the cupric ions to prevent oxidation of the dye in the absence of creatinine.

2. The method of claim 1 wherein the chelating agent is selected from those chelating agents which form a $Cu^{+2}$ complex with cupric ion which complex has a binding constant which is lower than that of creatinine with cupric ion but high enough to form a stable complex with the cupric ion.

3. The method of claim 1 wherein the chelating agent is citrate.

4. The method of claim 3 wherein the citrate to cuprous ion ratio is in the range of 0.5 to 3.5, the cupric ion concentration is from 5 to 80 mM and the citrate concentration is from 3 to 280 mM.

5. The method of claim 1 wherein the oxidizable dye is benzidine, o-tolidine; a 3,3',5,5'-tetraalkylbenzidine wherein the alkyl group includes from one to about six carbon atoms; o-dianisidine; 2,7-diaminofluorence; bis-(N-ethylquinol-2-one)-azine; (N-methylbenzthiazol-2-one)-(1-ethyl-3-phenyl-5-methyltriazole-2-one)-azine or combinations thereof.

6. The method of claim 1 wherein the hydroperoxide is cumene hydroperoxide, 5-butyl hydroperoxide, diisopropylbenzene hydroperoxide, 1-hydroxycyclohexane-1-hydroperoxide, 2,5-dimethylhexane-2,5-dihydroperoxide, paramenthane hydroperoxide, 1,4-diisopropylbenzene monohydroperoxide, p-5-butylisopropylbenzene hydroperoxide, 2-(α-hydroperoxyisopropyl)-6-isopropylnaphthalene, tetralin hydroperoxide or combinations thereof.

7. The method of claim 1 wherein the buffer is phosphate, glycerol-2-phosphate, maleic acid, 3-N-morpholinopropanesulfonic acid (MOPS), cacodylic acid, 3,3-dimethylglutaric acid, carbonic acid, 4-hydroxymethylimidazole, Bis-tris[bis-(2-hydroxyethyl)imino]-tris [(hydroxymethyl)methane], ortho-phosphorous acid, dimethylaminoethylamine, ADA (N-(2-acetamido) iminodiacetic acid, pyrophosphoric acid, N,N'-bis(3-sulphopropyl)ethylenediamine, piperazine-N,N'-bis(2-ethanesulphonic acid)), 1,3-bis[tris(hydroxymethyl) methylamino]propane, ethylenediamine, N-(2-acetamido)-2-aminoethanesulphonic acid, imidazole, (2-aminoethyl) trimethylammonium chloride, N,N-bis(2-hydroxyethyl)-2-aminoethanesulphonic acid, 3,6-endomethylene-1,2,3,6-tetrahydrophthalic acid, 2,3-dihydroxypropyl-tris-(hydroxymethyl)methylamine, 2,4,6-trimethylpyridine, N-tris(hydroxymethyl)methyl-2-aminoethanesulphonic acid, 4-methylimidazole, N-2-hydroxyethylpiperazine-N'-2-ethanesulphonic acid, N-ethylmorpholine, triethanolamine, mono-tris-2-hydroxyethylimino-tris (hydroxymethyl)methane, triisopropylamine, 5,5-diethylbarbituric acid, N-2-hydroxyethylpiperazinepropanesulphonic acid, glycylglycine, phenyl phosphate, nitrophenyl phosphate, naphthyl phosphate, diphenyl phosphate, phenyl phosphonic acid, aminoethyl phosphonic acid, ethyl phosphonic acid, carboxyethyl phosphonic acid, ethyl phosphate, aminoethyl phosphate, glycerol phosphate, phytic acid, 6-glucose phosphate, 1-glucose phosphate or a combination thereof.

8. The method of claim 1 wherein the concentration of buffer is from 250 to 1000 mM.

9. The method of claim 1 wherein the pH is maintained at a pH of from 6.7 to 7.4.

10. The method of claim 1 wherein the source of cupric ion is cupric sulfate.

11. The method of claim 1 wherein the oxidizable dye is 3,3',5,5'-tetramethylbenzidine (TMB), the hydroperoxide is diisopropylbenzene dihydroperoxide and the chelating agent is citrate.

12. A method of preparing a test device for the determination of the concentration of creatinine in urine which comprises:

a) contacting an absorbant carrier material with an aqueous solution of a cupric salt, a chelating agent and a buffer having a pKa in the range of 6.6 to 8.0 which, upon contact with a urine test sample is capable of maintaining the pH of the test sample within a range of 6.6 to 8.0 regardless of the specific gravity of the urine test sample by virtue of the buffer's pKa and concentration in the absorbant carrier material upon drying and drying the absorbant carrier material; and b) contacting the absorbant carrier material with an organic solution of an oxidizable dye and a hydroperoxide followed by drying of the absorbant carrier material.

13. The method of claim 12 wherein the cupric salt is cupric sulfate, the chelating agent is citrate, the buffer is glycerol-2-phosphate, the oxidizible dye is 3,3',5,5'-tetramethyl-benzidine and the hydroperoxide is diisopropylbenzene dihydroperoxide.

14. The method of claim 12 wherein the concentration of cupric ion in the aqueous solution is from 5 to 80 mM, the concentration of chelating agent is 3 to 280 mM, the concentration of the buffer is 250 to 1000 mM and the ratio of chelating agent to cupric ion is from 0.5 to 3.5.

15. A test strip for the determination of creatinine in urine prepared by the method of claims 12–14.

* * * * *